US008358125B2

(12) United States Patent
Moser et al.

(10) Patent No.: US 8,358,125 B2
(45) Date of Patent: Jan. 22, 2013

(54) METHOD FOR DETERMINING GEOMETRIC CHARACTERISTICS OF AN ANOMALY IN A TEST OBJECT AND MEASURING APPARATUS FOR CARRYING OUT THE METHOD

(75) Inventors: Roland Richard Moser, Zurich (CH); Bernard Revaz, Geneva (CH); Serge Reymond, Geneva (CH); Pavel Kejik, Ecublens (CH); Radivoje Popovic, St-Sulpice (CH)

(73) Assignee: ALSTOM Technology Ltd., Baden (CH)

( * ) Notice: Subject to any disclaimer, the term of this patent is extended or adjusted under 35 U.S.C. 154(b) by 968 days.

(21) Appl. No.: 12/260,184

(22) Filed: Oct. 29, 2008

(65) Prior Publication Data
US 2009/0108838 A1 Apr. 30, 2009

(30) Foreign Application Priority Data

Oct. 29, 2007 (CH) .................................... 1679/07

(51) Int. Cl.
*G01R 33/12* (2006.01)

(52) U.S. Cl. ... 324/216; 324/240; 324/222; 324/755.01; 324/228

(58) Field of Classification Search .................. 324/228, 324/235, 240, 242, 251, 216
See application file for complete search history.

(56) References Cited

U.S. PATENT DOCUMENTS

| 2002/0097045 | A1* | 7/2002 | Crouzen et al. ............... 324/240 |
| 2004/0257072 | A1* | 12/2004 | Samson ........................ 324/242 |
| 2005/0248339 | A1* | 11/2005 | Goldfine et al. ............... 324/240 |
| 2006/0186880 | A1* | 8/2006 | Schlicker et al. .............. 324/242 |
| 2007/0046287 | A1* | 3/2007 | Vervaeke et al. .............. 324/251 |

OTHER PUBLICATIONS

Dover, W. D., et al., "The Use of A-C Field Measurements to Determine the Shape and Size of a Crack in a Metal," Eddy-Current Characterization of Materials and Structures, 1981, pp. 401-427.
Gamage, S. K., et al., "A study on a silicon Hall effect device with an integrated electroplated planar coil for magnetic sensing applications," J. Micromech. Microeng. 2006, vol. 16, pp. 487-492, Inst. of Physics Publishing, United Kingdom.
Popovic, R.S., "Sensor Microsystems," Microelectronics, 1995, Proceedings., 1995 20th International Conference on NIS, pp. 531-537, Serbia Sep. 12-14, 1995, New York, NY, USA.

(Continued)

*Primary Examiner* — Jermele M Hollington
*Assistant Examiner* — Son Le
(74) *Attorney, Agent, or Firm* — Cermak Nakajima LLP; Adam J. Cermak

(57) ABSTRACT

In a method for determining geometrical characteristics (d) of an anomaly (12) which changes the electrical conductivity in the region near the surface of an electrically conducting, in particular a metallic test object (10), a considerable simplification is achieved in that, in the region of the anomaly (12) in the test object (10), eddy currents (13, 14) of different frequencies are excited, and the magnetic field ($B_{y,0}$), which is produced by the excited eddy currents, is scanned in the vicinity of the anomaly (12) and the geometric characteristics of the anomaly are exclusively deduced from the distribution of the magnetic field ($B_{y,0}$).

19 Claims, 4 Drawing Sheets

OTHER PUBLICATIONS

Popovic, R.S., "Hall Devices for Magnetic Sensor Microsystems," IEEE Transducers 1997, pp. 377-380, 1997 International Conference on Solid-State Sensors and Actuators, Jun. 16-19, 1997, Chicago, IL, US.

Sadeghi, S. H. H., et al., "Surface Potential Distributions Due to Eddy Currents Around Long Cracks in Metals, Induced by U-shaped Current-Carrying Wires," IEEE Transactions on Magnetics, IEEE Service Center, Bd. 27, Nr. 1, Jan. 1991, pp. 674-679, New York, NY, US.

Sadeghi, S. H. H., et al., "On the suitability of induction coils for crack detection and sizing in metals by the surface magnetic field measurement technique," NDT&E International 2001, vol. 34, Nr. 7, pp. 493-504, Butterworth-Heimann, Oxford, Great Britain.

Minkov, D., et al., "Method of sizing of 3-D surface breaking flaws by leakage flux," NDT&E International 1998, vol. 31, Nr. 5, pp. 317-324, Butterworth-Heimann, Oxford, Great Britain.

Sophian, A., et al., "Pulsed magnetic flux leakage techniques for crack detection and characterisation," Sensors and Actuators A 2006, vol. 125, Nr. 2, pp. 186-191, Elsevier Sequoia S.A., Lausanne, Switzerland.

Search Report for Swiss Patent App. No. 1679/2007 (Feb. 8, 2008).

Search Report for European Patent App. No. 08167754.4 (Feb. 9, 2008).

* cited by examiner

METHOD FOR DETERMINING GEOMETRIC CHARACTERISTICS OF AN ANOMALY IN A TEST OBJECT AND MEASURING APPARATUS FOR CARRYING OUT THE METHOD

This application claims priority under 35 U.S.C. §119 to Swiss application no. 01679/07, filed 29 Oct. 2007, the entirety of which is incorporated by reference herein.

BACKGROUND

1. Field of Endeavor

The present invention relates to the field of non destructive testing of test objects. It relates to a method for determining geometrical characteristics of an anomaly in a test object and to a measuring apparatus for carrying out the method.

2. Brief Description of the Related Art

Applicant is aware that the maximum of the surface plane quadrature component (out-of-phase component) of the crack-related magnetic field anomaly ($B_{y,0}''(\omega)$) in the alternating magnetic field of a crack which extends into an electrically conducting test object from the surface of the test object, contains useful information with respect to the geometry of the crack. The advantage of such a process is that the measured magnetic field variable primarily depends on the depth of the crack rather than on the crack volume, as is the case, for example, in a static magnetic field. However, the crack depth cannot be correlated with the measured $B_{y,0}''_{max}(\omega)$ without additionally knowing the skin depth and the magnetic permeability of the test object.

SUMMARY

One of numerous aspects the present invention includes methods and apparatus which can be used to determine the geometrical characteristics of an anomaly, in particular the depth of a crack, in an electrically conducting, in particular metallic, test object without having additional knowledge about the test object.

Another aspect of the present invention relates to excited eddy currents in the region of an anomaly in the test object and the scanning of the magnetic field, which is produced by the excited eddy currents, in the vicinity of the anomaly and the inferring of geometrical characteristics of the anomaly exclusively from the distribution of the magnetic field.

An exemplary embodiment of the method adhering to principles of the present invention can be characterized in that anomalies, in the form of cracks, are investigated, in that the crack depth is determined as the geometric characteristic of the cracks, in that in a first step the position of the crack on the surface of the test object is determined, and in that in a second step the distribution of the magnetic field transversely with respect to the longitudinal direction of the crack is scanned and evaluated, wherein the eddy currents in the region of the crack are excited by applying an alternating magnetic field, and the quadrature component, which is located in the plane of the surface and transversely with respect to the longitudinal direction of the crack, of the magnetic field is scanned and evaluated.

The quadrature component of the magnetic field is preferably scanned at different frequencies of the alternating magnetic field and evaluated, wherein in particular the frequency of the alternating magnetic field traverses a prespecified frequency range, from approximately 1 kHz to approximately 1 MHz.

Another exemplary embodiment of the method adhering to principles of the present invention can be characterized in that, starting from the crack, the first zero crossing of the quadrature component, which is located in the plane of the surface and transversely with respect to the longitudinal direction of the crack, of the magnetic field is determined and the maximum current layer width of the current layers, linked to the crack, of the eddy currents is ascertained from the first zero crossing, and in that the depth of the associated crack is deduced from the ascertained maximum current layer width.

For measuring the magnetic field, a measuring head operating on the basis of the Hall effect is preferably used, wherein in particular the measuring head comprises a plurality of sensor elements, which are arranged in a linear sensor array, on CMOS (complementary metal-oxide-semiconductor) basis in the form of vertical Hall elements. For measuring the quadrature component, which is located in the plane of the surface and transversely with respect to the longitudinal direction of the crack, of the magnetic field, the linear sensor array is here aligned transversely to the longitudinal direction of the crack.

The maximum current layer width is preferably determined with an accuracy of 10 µm and the crack depth with a resolution of approximately 50 µm.

Another exemplary embodiment of the measuring apparatus according to the invention can be characterized in that first means comprises a magnetic coil, in that second means comprises a measuring head arranged inside or below the magnetic coil, in that the magnetic coil and the measuring head are combined in a scanning apparatus, and in that the scanning apparatus can be moved over the surface of the test object, wherein the scanning apparatus can preferably be moved using a robot.

In particular, the magnetic coil is connected to a frequency generator generating frequencies in the range between approximately 1 kHz and approximately 1 MHz. The measuring head comprises a linear sensor array with sensor elements which operate according to the Hall effect and is connected to a signal processing unit. The sensor elements of the linear sensor array are here preferably configured on CMOS basis in the form of vertical Hall elements.

BRIEF DESCRIPTION OF THE DRAWINGS

The invention will be explained in more detail below with reference to exemplary embodiments in conjunction with the drawings, in which.

DETAILED DESCRIPTION OF EXEMPLARY EMBODIMENTS

Figure 1:
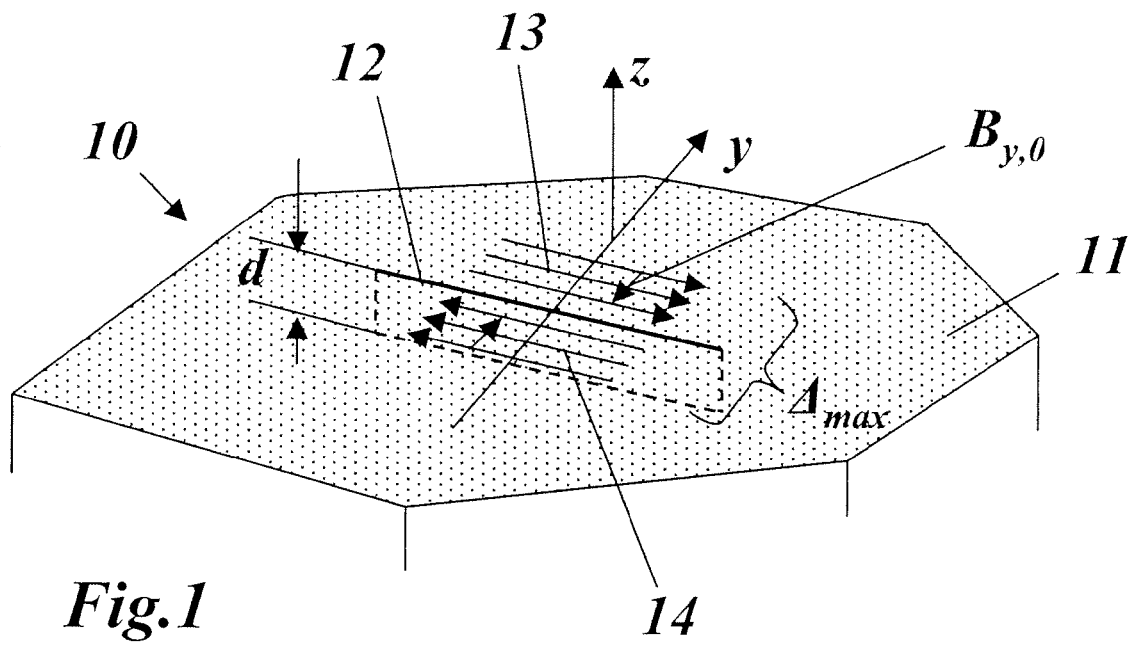
FIG. 1 shows, in a schematic representation, the initial situation in the method according to the invention, in which a crack, with a crack depth, extends from the surface into an electrically conducting test object and forms eddy currents with current layers when an alternating magnetic field is applied.

FIG. 1 shows, in a schematic representation, the typical initial situation in the method according to the invention. A test object 10 composed of an electrically conducting material, e.g., a metal, has a surface 11, whence a crack 12, with a crack depth d, extends into the test object. The crack 12 further extends in a longitudinal direction (x-direction in the coordinate system in FIG. 1). If an alternating magnetic field is now applied to the region of the test object 10 which contains the crack 12, eddy currents are induced in the test object 10 near the surface, which in turn produce a magnetic field. Current layers 13, 14, which are orientated by the profile of the crack 12 (the width of the current layers 13, 14 is shown in FIG. 1 in an exaggerated fashion), are formed in the region of the crack 12 which represents an insulating barrier for the eddy currents. The (alternating) current layers 13, 14 produce an (alternating) magnetic field, which influences the component $B_{y,0}$ in the plane of the surface 11, perpendicular to the longitudinal direction of the crack 12.

The current layer width $\Delta$ is a function of the crack depth d, the material properties of the test object 10, and the interrogating frequency $F_{int}$ of the eddy current. The dependency of current layer width $\Delta$ on the interrogating frequency $F_{int}$ is schematically shown for different materials material m1 to m5 in FIG. 2a for three different cracks: crack I to crack III. In all cases, the current layer width $\Delta$ is a continuous function of the interrogating frequency $F_{int}$ of the eddy current in the range $10^3$ Hz to $10^7$ Hz. These functions have only one maximum. As can be seen from all examples, the maximum current layer width $\Delta_{max}$ is independent of the material properties and is a characteristic value for each crack depth d. In other words, the same maximum current layer width $\Delta_{max}$ can be observed for a given crack depth d. However, the interrogating frequency $F_{int}$ for which the maximum current layer width $\Delta_{max}$ will be observed depends on the material properties. To find the maximum current layer width $\Delta_{max}$, the interrogating frequency $F_{int}$ has to varied over a wide frequency range, typically between $10^3$ Hz and $10^7$ Hz. This can be done as a continuous scan or with a stepwise variation of the interrogating frequency $F_{int}$. A stepwise variation of the frequency reduces the amount of data to be processed and allows a faster scan. Scanning processes with different step sizes are conceivable. For example, simple constant steps, or steps which are a fraction or multiple of the last interrogating step, can be used. Scanning can be stopped once the maximum current layer width $\Delta_{max}$ is identified.

Figure 2:
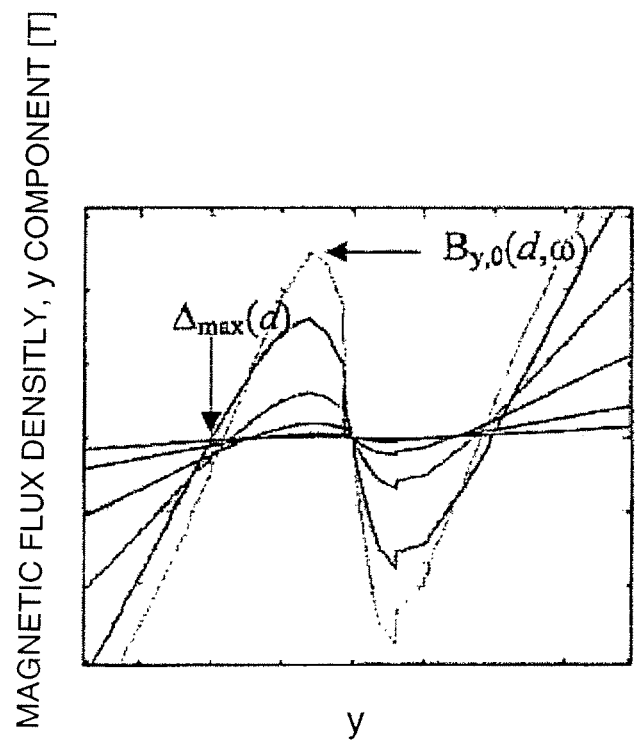
FIG. 2 shows the calculated curves of the quadrature component of the alternating magnetic field in the direction transverse to the crack for different frequencies of the alternating magnetic field.
Figure 2A:
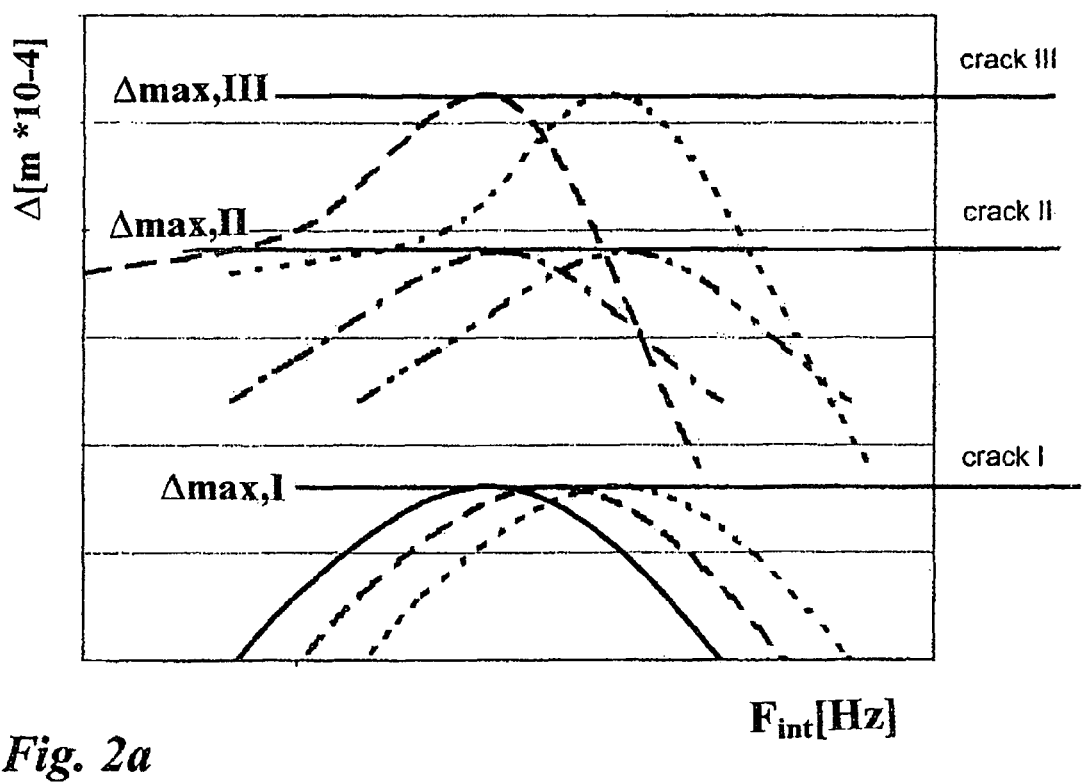
FIG. 2a shows the current layer width Δ as a function of the interrogating frequency.

In view of the dependency of the quadrature component portion $B_{y,0}''$ (y) on the y coordinate, the profile illustrated in FIG. 2, showing different curves for different frequencies of the exciting magnetic field (10 kHz, 30 khz, 100 kHz, 300 kHz, 1 Mhz, and 3 Mhz), can be produced. All of the shown curves (viewed from crack 12 at y=0) having a first zero crossing which is interpreted as width $\Delta$ of the current layers 13, 14. When viewed over the frequency range of the excitation frequency, ranging from 1 kHz to 1 MHz, the current layer width $\Delta$ passes through a maximum $\Delta_{max}$ dependent exclusively on the crack depth d and not on the electric conductivity and magnetic permeability of the material of which the test object 10 is made. The result is then, for the general case, the relationship presented in FIG. 3 between crack depth d and the maximum current layer width $\Delta_{max}$, which can be described in an approximate fashion by the proportionality relation $\Delta_{max} \sim d^{0.3}$. This relation forms a basis for the methods and apparatus described herein, which determines the crack depth d of a crack 12 by the measurement of the maximum current layer width $\Delta_{max}$ caused by the anomaly.

Figure 4A:
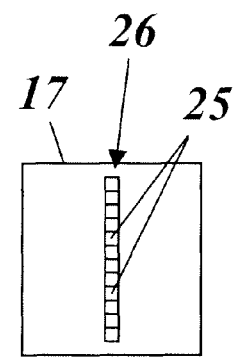
FIG. 4a shows the linear arrangement of VHD sensor elements of the scanning apparatus according to an exemplary embodiment of the invention.
Figure 4:
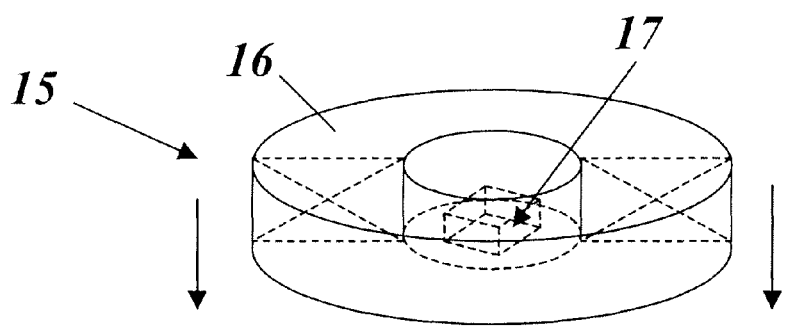
FIG. 4 shows an exemplary scanning apparatus for ascertaining the maximum current layer width at a crack.
Figure 4:
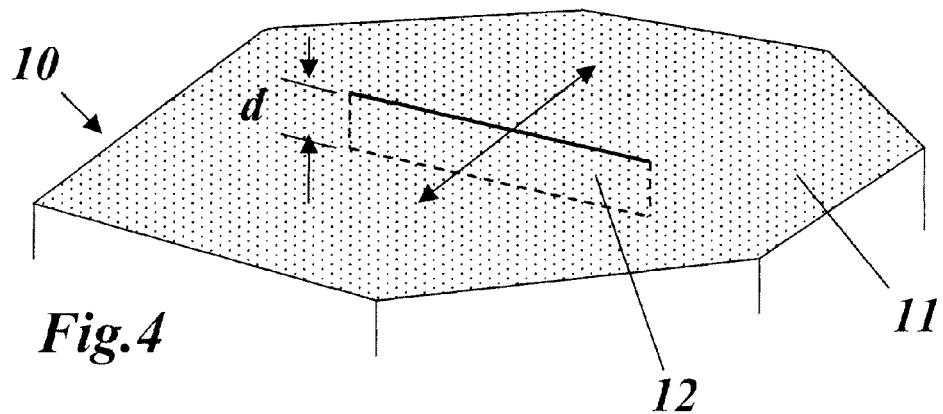
Figure 5:
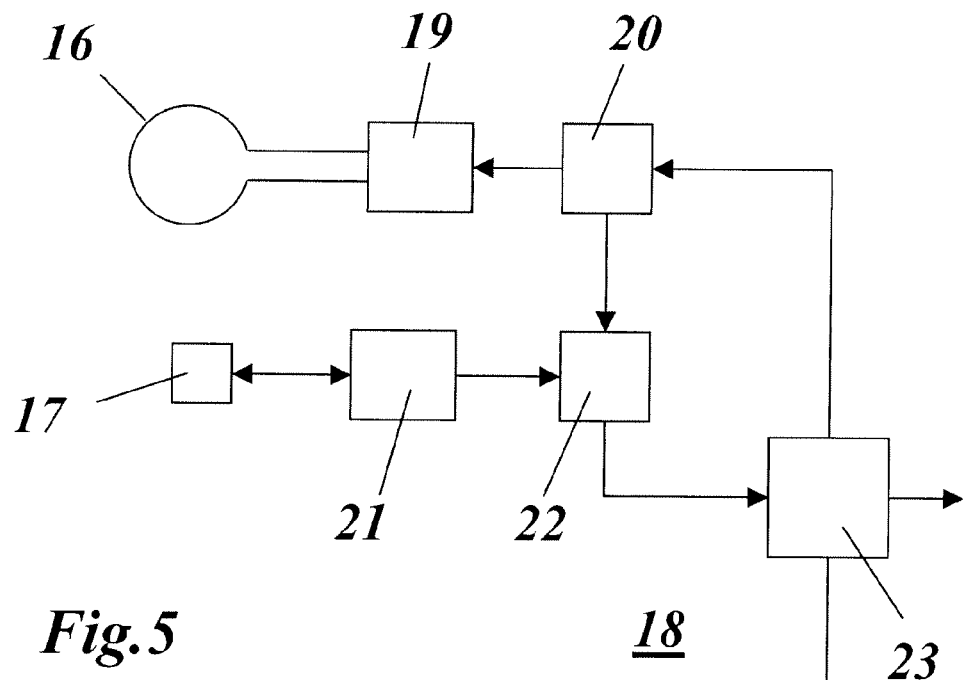
FIG. 5 shows a measuring apparatus, equipped with a robot, for determining the crack depth according to an exemplary embodiment of the invention.
Figure 5:
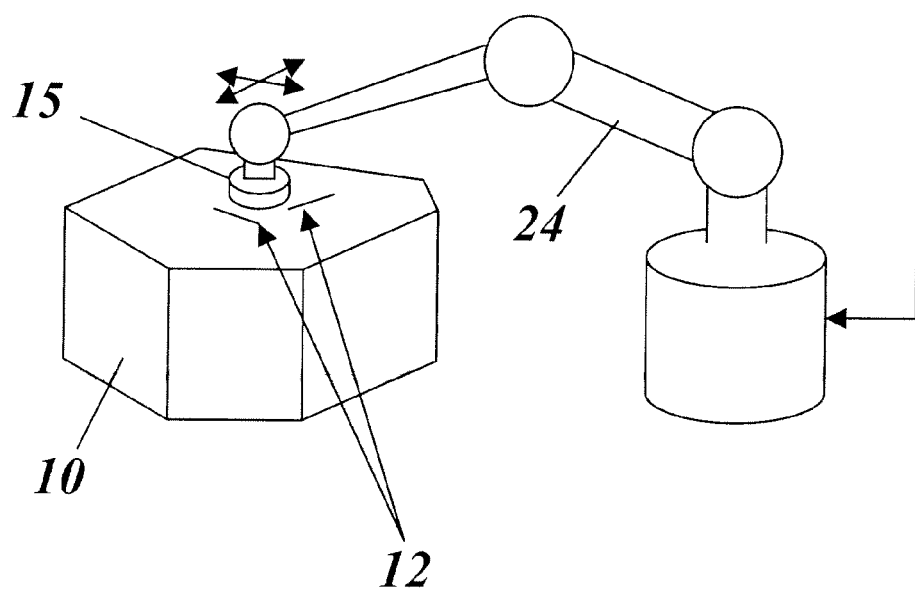

As shown in FIG. 4 and FIG. 5, the measuring apparatus 18 for measuring the crack depth includes a scanning apparatus 15 with a magnetic coil 16 having a frequency generator 20. The frequency generator 20 has a driver circuit 19 and is settable and tuneable to provide alternating current in the frequency range between 1 kHz and 10 MHz. The magnetic coil 16, which can for example have an external diameter of 4 mm and an internal diameter of 1.5 mm for determining crack depths of 1 mm or less, produces an alternating magnetic field which in turn produces eddy currents in the test object 10, used to interrogate the test object 10. Arranged inside or below the magnetic coil 16 is a measuring head 17 which is moved simultaneously with the magnetic coil 16 and which scans the magnetic fields produced by the eddy currents. At the core of the measuring head 17 is a semiconductor chip which is produced as per standard CMOS technology and contains a linear sensor array 26 of VHD sensor elements 25 (FIG. 4a) which are configured in the form of vertical Hall elements (Vertical Hall Devices: VHD).

This sensor array 26 can be used to measure the local components of the magnetic field in and outside of the plane of the surface 11. To achieve this the measuring head 17, and more specifically the sensor array 26, is connected to a sensor driving unit 21 which, among other things, applies a biasing voltage to the sensor array 26 and preamplifies the VHD signal. A signal processing unit 22, which is connected downstream of the frequency generator 20, demodulates and filters the signal. An evaluation unit 23 controls the frequency generator 20, evaluates the output signal of the signal processing unit 22 and controls a robot 24 (in the example of FIG. 5, a robot arm) which guides the scanning apparatus 15 with the magnetic coil 16 and the measuring head 17 over the surface 11 of the test object 10 under investigation. During the measurement, the robot 24 can move and rotate the scanning apparatus 15.

Using the measuring apparatus 18 shown in FIG. 5, an exemplary method can be carried out as follows:

1. Crack detection: with quick measurement technology, based on a change in the impedance, that is to say the resistance of the magnetic coil 16 and/or the presence of a peak in the component of the local magnetic field which is not in the surface plane, the presences of a crack is detected. During this process the robot 24 moves at a speed of, for example, 1 cm/s.

2. Positioning: if a crack is detected, the robot 24 stops. The sensor array 26 is then set in a position at right angles to the longitudinal direction of the crack.

Figure 3:
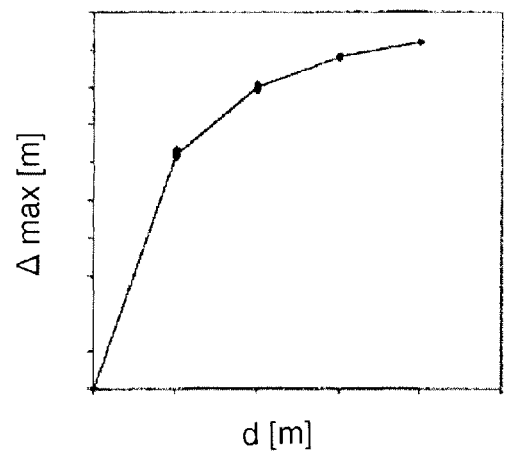
FIG. 3 shows the calculated relationship between the maximum current layer width determined from FIG. 2, with crack depth.

3. Determining the crack depth: in the set position, the excitation frequency of the magnetic coil is tuned, the zero crossing of $B_{y,0}''$(y) located, and the maximum current layer width $\Delta_{max}$ measured. From this the crack depth d, with the aid of the curve in FIG. 3, is determined.

An important factor in the present method can be the accuracy with which the position of the zero crossing of $B_{y,0}''$ (y) on the y-axis is determined. In order to achieve a resolution of the crack depth d of 50 μm at 1 mm, i.e., a resolution of 5%, $\Delta_{max}$ needs to be measured with an accuracy of 10 Δm. This can be achieved using a sensor array 26 with very closely packed VHD sensor elements 25, such as those developed at EPFL (Ecole Polytechnique Fédérale de Lausanne), Lausanne, Switzerland.

LIST OF REFERENCE SYMBOLS 10 test object (metallic)
11 surface (test object)
12 crack
13, 14 current layer
15 scanning apparatus
16 magnetic coil
17 measuring head
18 measuring apparatus
19 driver circuit
20 frequency generator
21 sensor driving unit
22 signal processing unit
23 evaluation unit
24 robot
25 VHD sensor element
26 sensor array
$B_{y,0}$ magnetic field (parallel to the surface, at right angles to the crack)
d crack depth
$\Delta$ current layer width
$\Delta_{max}$ maximum current layer width
$F_{int}$ Interrogating frequency While the invention has been described in detail with reference to exemplary embodiments thereof, it will be apparent to one skilled in the art that various changes can be made, and equivalents employed, without departing from the scope of the invention. The foregoing description of the preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A method for determining geometric characteristics of an anomaly in a region near the surface of an electrically conducting test object, the anomaly changing the electrical conductivity of the test object, the method comprising:
   exciting eddy currents of different frequencies in the region of the anomaly in the test object, to produce a magnetic field component $B_{y,0}$ which is perpendicular to a direction in which the anomaly extends along the test object;
   scanning said magnetic field component $B_{y,0}$ in the vicinity of the anomaly; and
   deducing the geometric characteristics of the anomaly exclusively from the distribution of the magnetic field component $B_{y,0}$;
   wherein said anomaly comprises at least one crack in the test object, and wherein deducing the geometric characteristics comprises determining a crack depth; and
   wherein determining a crack depth comprises first determining the position of the crack on the surface of the test object, and second scanning and evaluating the distribution of the magnetic field component $B_{y,0}$ transversely with respect to the longitudinal direction of the crack.

2. The method as claimed in claim 1, wherein exciting eddy currents comprises exciting eddy currents in the region of the crack by applying an alternating magnetic field; and scanning and evaluating comprises scanning and evaluating the quadrature component, which quadrature component is located in the plane of the surface and transversely with respect to the longitudinal direction of the crack, of the magnetic field.

3. The method as claimed in claim 2, wherein scanning comprises scanning the quadrature component of the magnetic field at different frequencies of the alternating magnetic field.

4. The method as claimed in claim 3, wherein scanning comprises scanning over a prespecified frequency range of the alternating magnetic field.

5. The method as claimed in claim 4, wherein the prespecified frequency range is from approximately 1 kHz to approximately 1 MHz.

6. The method as claimed in claim 2, comprising:
   determining, starting from the crack, the first zero crossing of the quadrature component, which first zero crossing is located in the plane of the surface and transversely with respect to the longitudinal direction of the crack, of the magnetic field;
   determining the maximum current layer width $\Delta_{max}$ of eddy current layers linked to the crack from the first zero crossing; and
   determining the depth of the associated crack from the determined maximum current layer width $\Delta_{max}$.

7. The method as claimed in claim 1, wherein scanning the magnetic field component $B_{y,0}$ comprises measuring with a Hall effect measuring head.

8. The method as claimed in claim 7, wherein the measuring head comprises a CMOS semiconductor chip having a plurality of sensor elements arranged in a linear sensor array as a vertical Hall detector.

9. The method as claimed in claim 8, wherein scanning comprises aligning the linear sensor array transversely with respect to the longitudinal direction of the crack, to measure the quadrature component of the magnetic field, the quadrature component located in the plane of the surface and transversely with respect to the longitudinal direction of the crack.

10. The method as claimed in claim 6, where determining the maximum current layer width $\Delta_{max}$ comprises determining with an accuracy of 10 μm and the crack depth with a resolution of approximately 50 μm.

11. The method as claimed in claim 1, wherein the test object is metallic.

12. A measuring apparatus useful for determining geometric characteristics of an anomaly in a region near the surface of an electrically conducting test object, the anomaly changing the electrical conductivity of the test object, the apparatus comprising:
   means for producing eddy currents of a prespecified frequency in the test object;
   means for measuring a magnetic field perpendicular to a direction in which the anomaly extends along the test object produced by said eddy currents, wherein said anomaly comprises at least one crack in the test object;
   means for deducing the geometric characteristics comprises determining a crack depth; and
   means for determining a crack depth including means for first determining the position of the crack on the surface of the test object, and means for second scanning and evaluating the distribution of the magnetic field component $B_{y,0}$ transversely with respect to the longitudinal direction of the crack.

13. The measuring apparatus as claimed in claim 12, wherein the means for producing eddy currents comprises a magnetic coil, and wherein the means for measuring a magnetic field comprises a measuring head arranged inside or below the magnetic coil.

14. The measuring apparatus as claimed in claim 13, further comprising:
a scanning apparatus configured and arranged to move over the surface of the test object, the scanning apparatus comprising the magnetic coil and the measuring head.

15. The measuring apparatus as claimed in claim 14, wherein the scanning apparatus is configured and arranged to be moved by a robot.

16. The measuring apparatus as claimed in claim 13, further comprising:
a frequency generator configured and arranged to generate frequencies in the range between approximately 1 kHz and approximately 1 MHz; and
wherein the magnetic coil is connected to the frequency generator.

17. The measuring apparatus as claimed in claim 13, further comprising:
a signal processing unit;
wherein the measuring head comprises a linear sensor array having Hall effect sensor elements; and
wherein the measuring head is connected to the signal processing unit.

18. The measuring apparatus as claimed in claim 17, wherein the sensor elements comprise CMOS vertical Hall elements.

19. A measuring apparatus operable to measure the depth of a surface crack or of a surface inhomogeneity in the magnetic permeability of a test object, the apparatus comprising:
a magnetic coil, and an electronic chip comprising an array of vertical Hall devices;
wherein the vertical Hall devices are arranged in at least one row along a straight line in or at one end face of the magnetic coil;
wherein the magnetic coil is configured and arranged to be driven by an alternating current generating an interrogating magnetic field of an interrogating frequency $F_{int}$ and generating eddy currents in the test object;
wherein the magnetic coil and the vertical Hall devices are together configured and arranged to deduce geometric characteristics of the surface crack or surface inhomogeneity, including to determine a crack depth; and
wherein the magnetic coil and the vertical Hall devices are together configured and arranged to first determine the position of the surface crack or surface inhomogeneity on the test object, and to second scan and evaluate the distribution of the magnetic field component $B_{y,0}$ transversely with respect to the longitudinal direction of the crack.

* * * * *